(12) United States Patent
Han et al.

(10) Patent No.: US 11,166,534 B2
(45) Date of Patent: Nov. 9, 2021

(54) SHAVING AID APPLICATION APPARATUS

(71) Applicant: DORCO CO., LTD., Seoul (KR)

(72) Inventors: Da Woon Han, Seoul (KR); Jong Jin Jeong, Seoul (KR); Byung Sun Ahn, Seoul (KR)

(73) Assignee: DORCO CO., LTD., Seoul (KR)

( * ) Notice: Subject to any disclaimer, the term of this patent is extended or adjusted under 35 U.S.C. 154(b) by 10 days.

(21) Appl. No.: 16/745,166

(22) Filed: Jan. 16, 2020

(65) Prior Publication Data
US 2020/0245740 A1 Aug. 6, 2020

(30) Foreign Application Priority Data

Feb. 1, 2019 (KR) .................. 10-2019-0013412

(51) Int. Cl.
*A45D 27/02* (2006.01)
*A61K 8/04* (2006.01)
*B05B 1/02* (2006.01)
*B65D 83/30* (2006.01)
*A61Q 9/02* (2006.01)

(52) U.S. Cl.
CPC .............. *A45D 27/02* (2013.01); *A61K 8/046* (2013.01); *B05B 1/02* (2013.01); *B65D 83/30* (2013.01); *A61Q 9/02* (2013.01)

(58) Field of Classification Search
CPC ...... A45D 27/02; B05B 1/1645; B05B 1/1654
See application file for complete search history.

(56) References Cited

U.S. PATENT DOCUMENTS

| 2,897,526 | A | * | 8/1959 | Norman | .................. | A45D 27/10 |
| | | | | | | 401/266 |
| 3,032,803 | A | * | 5/1962 | Joseph | .................. | B65D 83/285 |
| | | | | | | 401/190 |
| 3,263,744 | A | * | 8/1966 | Mackeown | ............ | B65D 83/72 |
| | | | | | | 165/47 |
| 3,672,546 | A | * | 6/1972 | Ruhle | .................... | B65D 83/30 |
| | | | | | | 222/402.12 |
| 3,795,366 | A | * | 3/1974 | McGhie | ............. | B65D 83/7532 |
| | | | | | | 239/397 |

(Continued)

FOREIGN PATENT DOCUMENTS

| EP | 1022235 | 7/2000 | | |
| EP | 1726538 | 11/2006 | | |
| FR | 2588490 | * 4/1987 | ............. | B05B 7/006 |

OTHER PUBLICATIONS

European Patent Office Application Serial No. 20154677.7, Search Report dated Jul. 3, 2020, 7 pages.

*Primary Examiner* — J C Jacyna
(74) *Attorney, Agent, or Firm* — Lee, Hong, Degerman, Kang & Waimey PC

(57) ABSTRACT

A shaving aid application apparatus is disclosed. According to at least one embodiment of the present disclosure, the apparatus includes a containing portion configured to hold a shaving aid; a head coupled to one side of the containing portion, an aid applying surface formed at one surface of the head; and multiple jetting holes located at the aid applying surface. A spraying gap is defined between at least a portion of the containing portion and at least a portion of the head, and the shaving aid is expelled from the containing portion to pass through the spraying gap and provided through the multiple jetting holes.

11 Claims, 11 Drawing Sheets

(56) References Cited

U.S. PATENT DOCUMENTS

| | | | |
|---|---|---|---|
| 5,385,303 A * | 1/1995 | Gosselin | B05B 1/1645 |
| | | | 239/394 |
| 5,687,485 A | 11/1997 | Shurtleff et al. | |
| 5,761,814 A | 6/1998 | Anderson et al. | |
| 5,813,785 A * | 9/1998 | Baudin | B65D 83/285 |
| | | | 401/190 |
| 5,956,848 A | 9/1999 | Tseng et al. | |
| 5,956,851 A | 9/1999 | Apprille et al. | |
| 6,041,926 A | 3/2000 | Petricca et al. | |
| 6,052,903 A | 4/2000 | Metcalf et al. | |
| 6,185,822 B1 | 2/2001 | Tseng et al. | |
| 6,212,777 B1 | 4/2001 | Gilder et al. | |
| 6,442,839 B1 | 9/2002 | Tseng et al. | |
| 6,516,518 B1 | 2/2003 | Garraway et al. | |
| 6,612,040 B2 | 9/2003 | Gilder | |
| 6,684,513 B1 | 2/2004 | Clipstone et al. | |
| 6,688,317 B2 | 2/2004 | Gueret | |
| 2011/0284586 A1* | 11/2011 | Kerr | A45D 19/02 |
| | | | 222/190 |
| 2014/0371690 A1 | 12/2014 | Sprada et al. | |
| 2016/0325916 A1 | 11/2016 | Jasper et al. | |

* cited by examiner (a)

(b)

SHAVING AID APPLICATION APPARATUS

CROSS-REFERENCE TO RELATED APPLICATIONS

Pursuant to 35 U.S.C. § 119(a), this application claims the benefit of earlier filing date and right of priority to Korean Patent Application No. 10-2019-0013412, filed on Feb. 1, 2019, the contents of which are hereby incorporated by reference herein in its entirety.

TECHNICAL FIELD

The present disclosure relates to a shaving aid application apparatus.

BACKGROUND

The statements in this section merely provide background information related to the present disclosure and do not necessarily constitute prior art.

When a wet razor is used, there are several factors that may create an inconvenience for a user.

For example, frictional force generated between a blade housing and the skin, cutting force applied to hair, irritation to a wounded skin area, etc. may create an inconvenience for the user.

To mitigate such inconvenience, shaving aids such as shaving foams, shaving gels, and shaving creams are used.

The shaving aid contains a lubricating ingredient and may be applied to the user's skin before shaving. This can reduce irritation to the skin when shaving is performed.

Shaving aids held in containers, such as cylindrical cans, are distributed and sold on the market. Generally, the user can use the shaving aid in its container by spraying the shaving aid out of the container, and then applying it to the skin.

However, in general, shaving aid in the conventional shaving aid container is sprayed onto the user's hand or brush first, and then the sprayed shaving aid is applied to an area of the skin to be shaved, thus negating the benefit of the shaving aid to the user.

For example, when a conventional shaving aid container is used, the hands may get dirty by the shaving aid spayed onto the hands.

In addition, applying the shaving aid to the skin by using an unclean hand or brush may cause a sanitary issue such that that bacteria, foreign substances, etc., residing on the hand or brush are transferred to the skin.

In addition, the steps involving spraying the shaving aid to the hand or brush and applying the sprayed shaving aid to the skin add to the intricate maneuver of the user, until the application of the shaving aid.

SUMMARY

In accordance with at least one embodiment, the present disclosure provides an apparatus for applying a shaving aid, the apparatus including a containing portion configured to hold a shaving aid; a head coupled to one side of the containing portion, an aid applying surface formed at one surface of the head; and multiple jetting holes located at the aid applying surface. A spraying gap is defined between at least a portion of the containing portion and at least a portion of the head. The shaving aid is expelled from the containing portion to pass through the spraying gap and provided through the multiple jetting holes.

DETAILED DESCRIPTION

Figure 1:
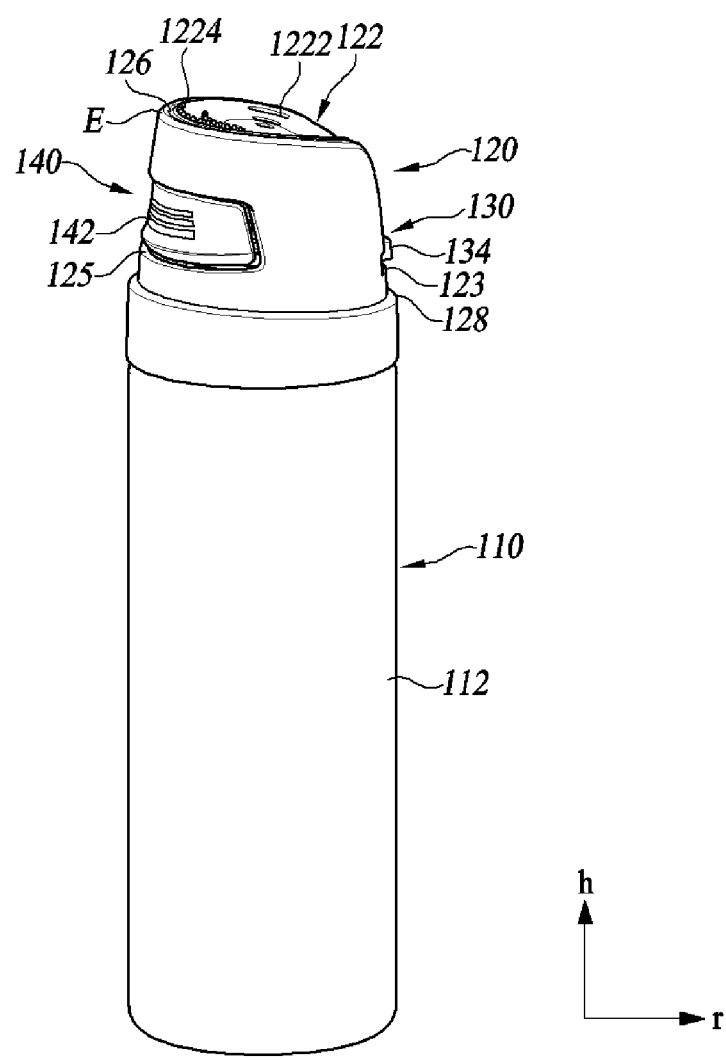
FIG. 1 is a front perspective view of a shaving aid application apparatus according to one embodiment of the present disclosure.

The present disclosure in at least one embodiment aims to provide a shaving aid application apparatus configured to apply a shaving aid in direct contact with the user's skin, thereby providing the user with a cleaner and easier application of the shaving aid.

Hereinafter, some embodiments of the present disclosure will be described in detail with reference to the accompanying drawings. In the following description, like reference numerals designate like elements, although the elements are shown in different drawings. Further, in the following description of some embodiments, a detailed description of known functions and configurations incorporated therein will be omitted for the purpose of clarity and for brevity.

In describing the components of the embodiments according to the present disclosure, various terms such as first, second, i), ii), a), b), etc., may be used solely for the purpose of differentiating one component from the other, not to imply or suggest the substances, the order or sequence of the components. Throughout this specification, when a part "includes" or "comprises" a component, the part is meant to further include other components, not to exclude thereof unless specifically stated to the contrary.

FIG. 1 is a front perspective view of a shaving aid application apparatus 10 according to one embodiment of the present disclosure.

Figure 2:
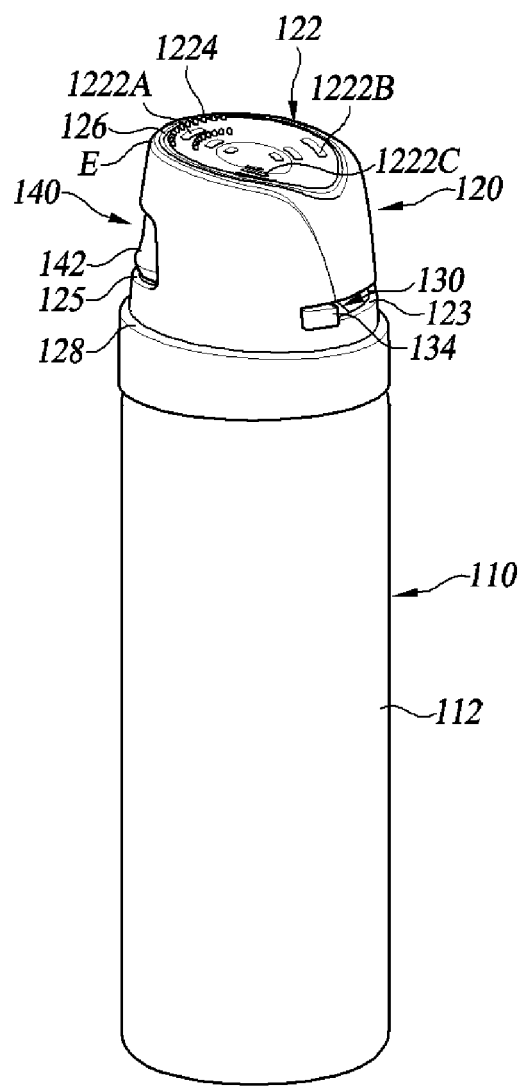
FIG. 2 is a rear perspective view of a shaving aid application apparatus according to one embodiment of the present disclosure.

FIG. 2 is a rear perspective view of a shaving aid application apparatus 10 according to one embodiment of the present disclosure.

As shown in FIG. 1 and FIG. 2, the shaving aid application apparatus 10 includes a containing portion 110, a head 120, a jetting region adjusting portion 130, and a spraying actuating portion 140.

The containing portion 110 receives a compressed shaving aid.

The shaving aid contained in the containing portion 110 may be in a liquid phase in a compressed state.

The liquid shaving aid may expand rapidly when sprayed from a spraying portion 116 (shown in FIG. 3) of the containing portion 110, thereby, being transformed into a foam substance that is easy to apply.

However, the shaving aid of the present disclosure is not limited thereto. For example, the shaving aid may be a material such as gel or cream. In this case, the shaving aid may be expelled from the containing portion 110 simply by a pumping member, regardless of compression or expansion.

The head 120 may be disposed on one side of the containing portion 110.

The head 120 may have one surface formed with an aid applying surface 122.

The aid applying surface 122 is an area where the shaving aid is applied by directly contacting or facing the user's skin when the application apparatus 10 is used.

The shaving aid application apparatus 10 according to one embodiment of the present disclosure features a configuration for applying the shaving aid to the user's skin by directly contacting or facing the application apparatus 10 to the user's skin after the shaving aid is expelled from the containing portion 110.

The shaving aid application apparatus 10 according to one embodiment of the present disclosure has an advantage of applying the shaving aid more cleanly, obviating the need for the user's hand or brush to contact the skin during the application process.

In addition, the shaving aid application apparatus 10 according to one embodiment has multiple jetting holes 1222 for allowing the shaving aid to be expelled directly to the skin, thus not requiring the process of spraying the shaving aid to the user's hand or brush, whereby facilitating simple application of the shaving aid with less movements and steps.

The aid applying surface 122 may have an inclination with respect to a virtual plane (VP of FIG. 4) perpendicular to the height direction (h-axis direction of FIG. 1) of the containing portion 110.

This inclination can prevent the hand holding the application apparatus 10 from being excessively bent when the user operates the application apparatus 10.

In addition, this inclination may form an edge area E having a relatively small angle between the side of the head 120 and the aid applying surface 122.

The edge area E may provide convenience to the user when applying the shaving aid to a relatively narrow area, such as an area under a nose.

At least a portion of the aid applying surface 122 may have a concave surface having the multiple jetting holes 1222.

The concave surface may have a profile similar to the skin region where the application is made, through which the aid applying surface 122 may be in more smooth contact with the user's skin.

At least a portion of the concave surface may be made of an elastic rubber material. In this case, the concave surface may morph within the elastic range of the rubber material.

Therefore, the concave surface has an effect of improving contact with the user's skin by changing the shape following the contour of the user's face or skin to be applied with the aid through elastic deformation of the rubber material.

In addition, the use of the shaving aid application apparatus 10 with a soft rubber material provides a soft touch to the user.

The shaving aid accommodated in the containing portion 110 may be expelled to the outside through the multiple jetting holes 1222 formed in the concave surface.

The multiple jetting holes 1222 may be distributed over the concave surface, whereby the shaving aid may be evenly expelled in a wider area.

The concave surface is to take advantage of the concave shape for causing the shaving aid expelled from the multiple jetting holes 1222 to gather into the central region of the concave surface. In this way, the ejected shaving aid can be prevented from flowing down from the aid applying surface 122.

The concave surface may include a comb portion 1224 having a plurality of protrusions. The comb portion 1224 may be located at a rear portion on the aid applying surface 122 with respect to the application direction.

The comb portion 1224 is adapted to groom the user's hair during application of the shaving aid prior to shaving, thus achieving more effective hair cutting during subsequent shaving.

Figure 4:
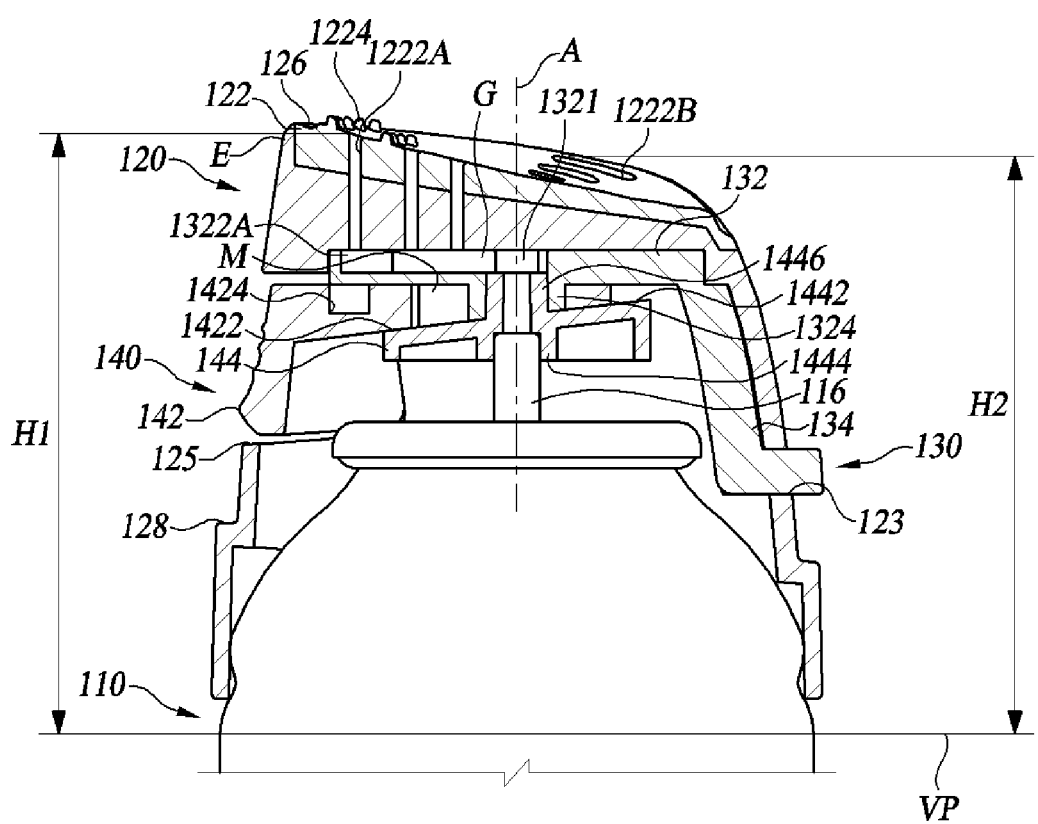
FIG. 4 is a side cross-sectional view of a spraying actuating portion of a shaving aid application apparatus in a rest position according to one embodiment of the present disclosure.

At least a portion of the containing portion 110 and at least a portion of the head 120 may form a spraying gap 'G' (shown in FIG. 4). The shaving aid delivered from the containing portion 110 may be led to the multiple jetting holes 1222 via the spraying gap 'G'.

Here, the spraying gap 'G' refers to an area between the spraying portion 116 (shown in FIG. 3) and the multiple jetting holes 1222 of the containing portion 120 on the flow path of the shaving aid.

The head 120 may include a first prevention protrusion 126 and a second prevention protrusion 128.

The first prevention protrusion 126 may be configured to prevent at least a portion of the shaving aid expelled from the multiple jetting holes 1222 from flowing out of the aid applying surface 122.

For this purpose, the first prevention protrusion 126 may have a step that surrounds the aid applying surface 122.

The second prevention protrusion 128 may be configured to prevent at least a portion of the shaving aid flowing from the aid applying surface 122 from further flowing down to the outer circumferential surface of the containing portion 110.

For this purpose, the second prevention protrusion 128 may include a step that surrounds the outer circumferential surface of the head 120 below the first prevention protrusion 126.

A recess may be formed on the horizontal area of the step of each of the first and second prevention protrusions 126 and 128. The shaving aid can be prevented from dripping from the first and second prevention protrusions 126, 128 by pooling in the recesses.

The jetting region adjusting portion 130 may be disposed in the spraying gap 'G', and configured to select a jetting hole for expelling the shaving aid and a jetting hole not expelling the shaving aid among the multiple jetting holes 1222.

This allows the jetting region adjusting portion 130 to selectively adjust the amount of shaving aid expelled from the multiple jetting holes 1222, or the region where the shaving aid is expelled on the aid applying surface 122.

The spraying actuating portion 140 may adjust the shaving aid spraying operation, and may have a spraying position and a rest position.

When the spraying actuating portion 140 is in the spraying position, the shaving aid may be expelled through the jetting holes 1222 from the spraying portion 116 (shown in FIG. 3) of the containing portion 110.

In contrast, when the spraying actuating portion 140 is in the rest position, the shaving aid is not allowed to be expelled from the spraying portion 116 of the containing portion 110.

The manner of spraying the shaving aid may be such that a single actuation to the spraying position sprays a predetermined amount of the shaving aid, but the present disclosure is not limited thereto.

For example, the spraying of the shaving aid may be continued until the spraying actuating portion 140 departs from the spraying position.

Figure 3:
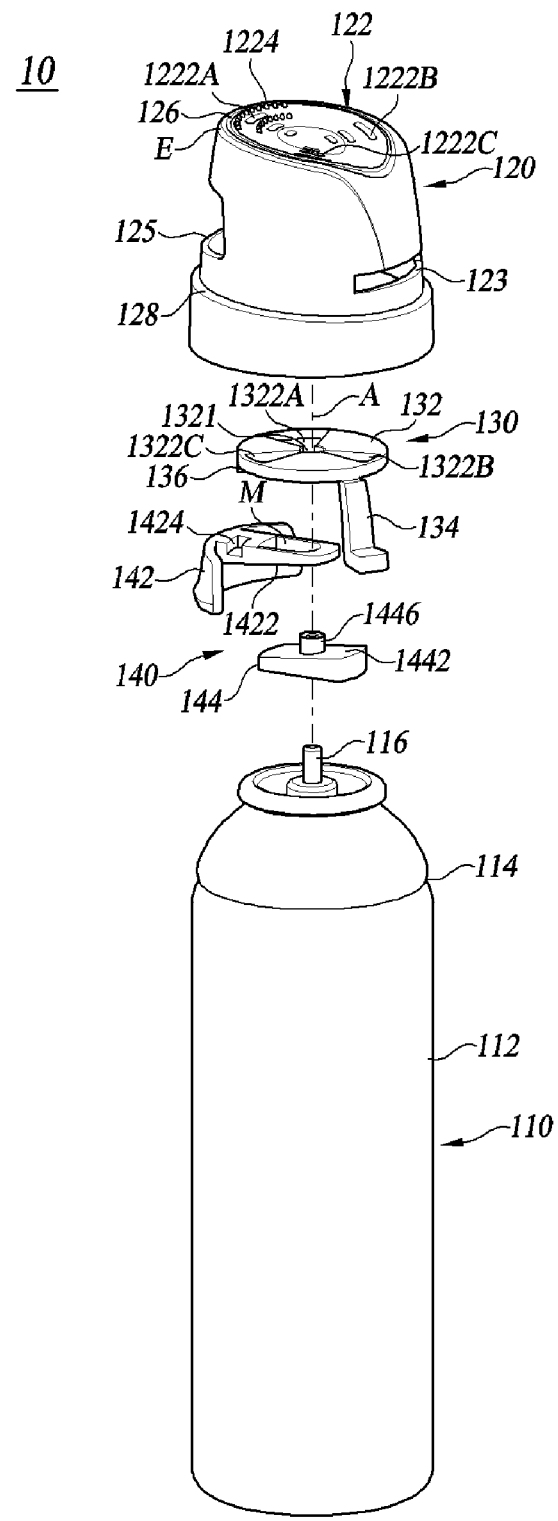
FIG. 3 is an exploded perspective view of a shaving aid application apparatus according to one embodiment of the present disclosure.

Detailed description of the respective aforementioned components is provided in relation to FIG. 3.

FIG. 3 is an exploded perspective view of a shaving aid application apparatus 10 according to one embodiment of the present disclosure.

As shown in FIG. 3, the containing portion 110 may include a main body 112, a connecting groove 114, and the spraying portion 116.

The body 112 may contain a compressed shaving aid therein and provide the user with a gripping area when the application apparatus 10 is used.

The body 112 may have a cylindrical shape so that the user can easily grip it, but the present disclosure is not limited thereto.

The connecting groove 114 may be disposed on the outer circumferential surface of the body 112 and may be fitted with a connecting protrusion (not shown) on the inner circumferential surface of the head 120. In this way, the containing portion 110 and the head 120 may be coupled to each other.

However, the present disclosure is not limited thereto, and a connecting protrusion formed on the outer circumferential surface of the containing portion 110 may be fitted into a connecting groove formed on the inner circumferential surface of the head 120.

The spraying portion 116 may be an area from which the shaving aid accommodated in the main body 112 is sprayed to the outside of the containing portion 110.

Accordingly, a spray nozzle (not shown) may be disposed on a free end (not shown) of the spraying portion 116.

The liquid shaving aid may be expanded rapidly while being sprayed from the spraying portion 116 to form bubbles.

The head 120 may include a first opening 123 and a second opening 125 at a side surface of the head 120.

The jetting region adjusting portion 130 may have a lever 134 which is at least partially exposed to the outside of the head 120 through the first opening 123. The spraying actuating portion 140 may have a button portion 142 which is at least partially exposed to the outside of the head 120 through the second opening 125.

The jetting region adjusting portion 130 may include a disk 132, the lever 134, and a locking protrusion 136.

The disk 132 may be disposed in the spraying gap 'G', and may rotate about a rotation axis 'A'.

The disk 132 may include a central channel 1321, multiple flow channels 1322A-1322C, and a first receiving portion 1324 (shown in FIG. 4).

The central channel 1321 may be located at a center portion of the disk 132 and may communicate with the first receiving portion 1324.

The first receiving portion 1324 may extend from the bottom surface of the disk 132.

The first receiving portion 1324 may accommodate a protruded portion 1444 of the pumping portion 144, and for this purpose, the first receiving portion 1324 may be grooved to correspond to the protruding portion 1444.

The multiple flow channels 1322A-1322C may branch from the central channel 1321, and the shaving aids expelled from the spraying portion 116 may be branched from the central channel 1321 and delivered into each of the flow channels 1322A-1322C.

The shaving aid delivered to the flow channels 1322A-1322C may be delivered to one or more jetting holes 1222 with which each of the flow channels 1322A-1322C communicates.

The lever 134 may extend from one side of the disk 132, and at least a portion of the lever 134 may be exposed to the outside through the first opening 123 of the head 120.

The user may rotate the disk 132 by operating the lever 134.

For example, the user may rotate the disk 132 by rotating the exposed area of the lever 134 in the circumferential direction of the rotation axis 'A'.

The locking protrusion 136 may protrude from the bottom surface of the disk 132.

The locking protrusion 136 may have a shape corresponding to the spraying actuating portion 140 at its provided locking groove 1424, and thus, it may be inserted into or removed from the locking groove 1424.

When at least a portion of the locking projection 136 is inserted into the locking groove 1424, the spraying actuating portion 140 is locked into the rest position.

On the contrary, when the locking protrusion 136 is completely released from the locking groove 1424, the spraying actuating portion 140 may be released from the locked state, and may be movable relative to the head 120.

Locking of the spraying actuating portion 140 using the locking projection 136 may be made through the rotation of the disk 132, which may be made through the operation of the lever 134.

The spraying actuating portion 140 may include the button portion 142 and the pumping portion 144.

The button portion 142 may have a first inclined surface 1422 on one surface thereof, and may move in a first direction with respect to the head 120.

The pumping portion 144 may have a second cam surface or second inclined surface 1442 configured to produce a cam motion with the first inclined surface 1422.

The button portion 142 moving in the first direction causes the cam motion between the first inclined surface 1422 and the second inclined surface 1442.

Thanks to the cam action between the first inclined surface 1422 and the second inclined surface 1442, the pumping portion 144 may move in a second direction which is not parallel to the first direction with respect to the head 120.

The first direction may be perpendicular to the height direction of the containing portion 110, and the second direction may be parallel to the height direction of the containing portion 110, although the present disclosure is not limited thereto.

The pumping portion 144 may include a second receiving portion 1444 (shown in FIG. 4) and a protrusion 1446.

The second receiving portion 1444 may accommodate the spraying portion 116 of the containing portion 110, and for this purpose, it may have a groove shaped to correspond to the spraying portion 116.

The protrusion 1446 may extend from an upper surface of the pumping portion 144, and may have a hollow therein communicating with the second receiving portion 1444.

The protrusion 1446 may be received in the first receiving portion 1324 of the disk 132.

The first receiving portion 1324 and the protrusion 1446 may be accommodated in a moving space 'M' of the button portion 142. In addition, the moving space M may have a free space in the first direction with the pumping portion 144 and the first receiving portion 1324 accommodated.

This allows the button portion 142 to move in the first direction without being interfered by the first receiving unit 1324 and the protrusion 1446.

The area of the button portion 142, which is exposed to the second opening 125, may be located on the side of the head 120 adjacent to the edge area 'E'.

As a result, the user can conveniently perform the spraying operation while holding the shaving aid application apparatus 10.

FIG. 4 is a side cross-sectional view of a spraying actuating portion 140 in a rest position according to one embodiment of the present disclosure.

Figure 5:
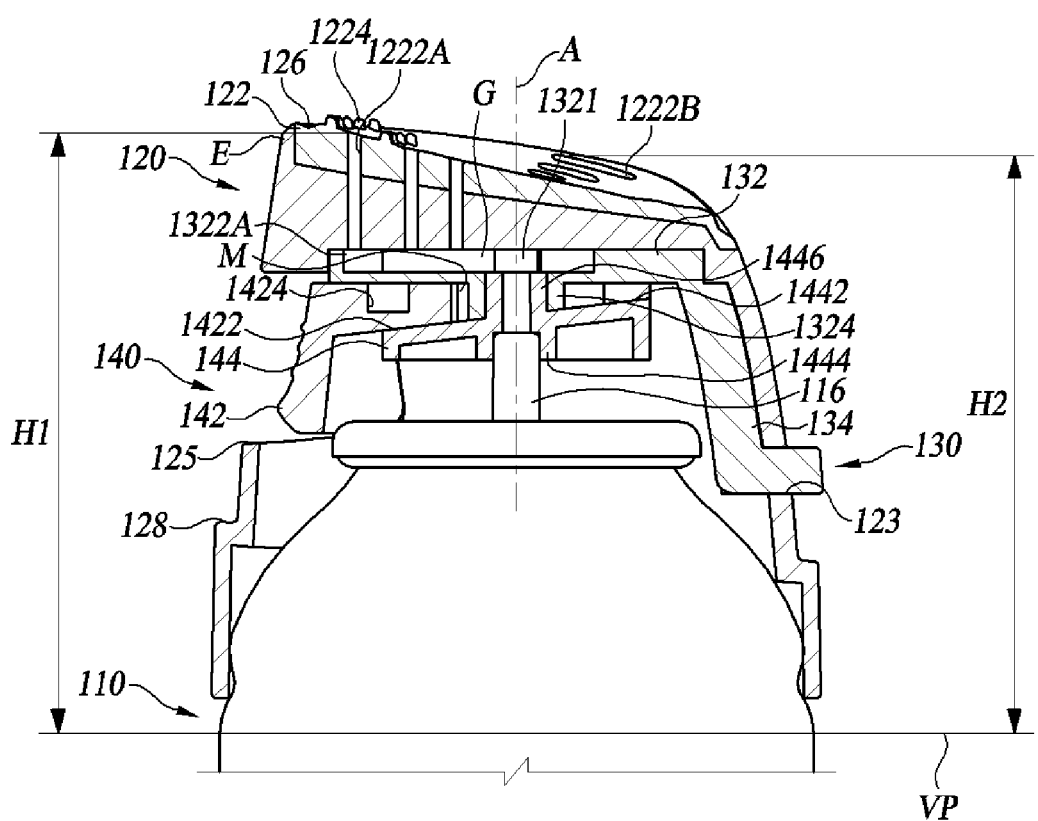
FIG. 5 is a side cross-sectional view of a spraying actuating portion of a shaving aid application apparatus in a spraying position according to one embodiment of the present disclosure.

FIG. 5 is a side cross-sectional view of a spraying actuating portion 140 in a spraying position according to one embodiment of the present disclosure.

The following describes in detail with reference to FIGS. 4 and 5, the manner of operating the spraying actuating portion 140 according to one embodiment of the present disclosure.

As shown in FIG. 4, at least a part of the button portion 142 of the spraying actuating portion 140 in a rest position may be exposed to the outside through the second opening 125 of the head 120.

Here, the user can move the button portion 142 to the inside of the head 120 along the first direction by pressing the exposed portion of the button portion 142 out of the rest position.

As shown in FIG. 5, the button portion 142 may move from its rest position into the head 120 in the first direction.

With the first receiving portion 1324 and the protruding portion 1446 accommodated by a wide margin in the moving space M, they do not interfere with the movement of the button portion 142 in the first direction.

When the button portion 142 moves in the first direction, the first inclined surface 1422 of the button portion 142 is in contact with the second inclined surface 1442 of the pumping portion 144, resulting in a cam action.

By this cam action, the pumping portion 144 may move in a second direction that is not parallel to the first direction.

As the pumping portion 144 moves in the second direction, the second receiving portion 1444 will press the free end of the spraying portion 116 and allow the shaving aid compressed in the containing portion 110 to be expelled from the spraying portion 116.

An elastic member (not shown) may be disposed in the head 120. The elastic member may exert an elastic force externally of the head 120 along the first direction with respect to the button portion 142 positioned at the spraying position.

By this elastic force, the position of the button portion 142 can be restored to the rest position.

Figure 6:
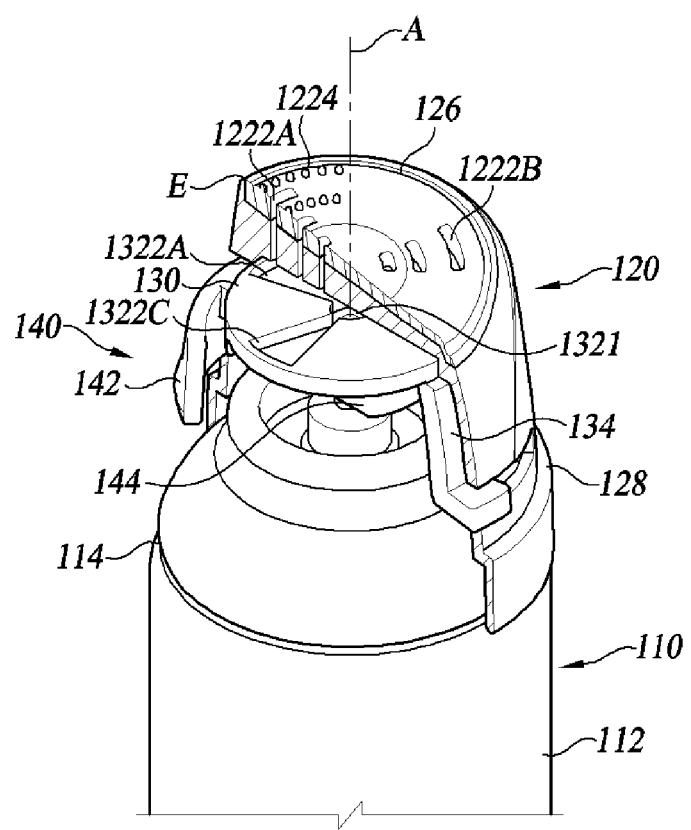
FIG. 6 is a partial cross-sectional view of a shaving aid application apparatus according to one embodiment of the present disclosure.

FIG. 6 is a partial cross-sectional view of a shaving aid application apparatus 10 according to one embodiment of the present disclosure.

As shown in FIGS. 5 and 6, the shaving aid expelled from the spraying portion 116 may be transferred to the central channel 1321 of the disk 132 through the internal hollow of the protrusion 1446.

The shaving aid transferred to the central channel 1321 is delivered to the multiple flow channels 1322A-1322C branched from the central channel 1321, and is ejected to the outside through the multiple jetting holes 1222 communicating with each of the flow channels 1322A-1322C.

Figure 7:
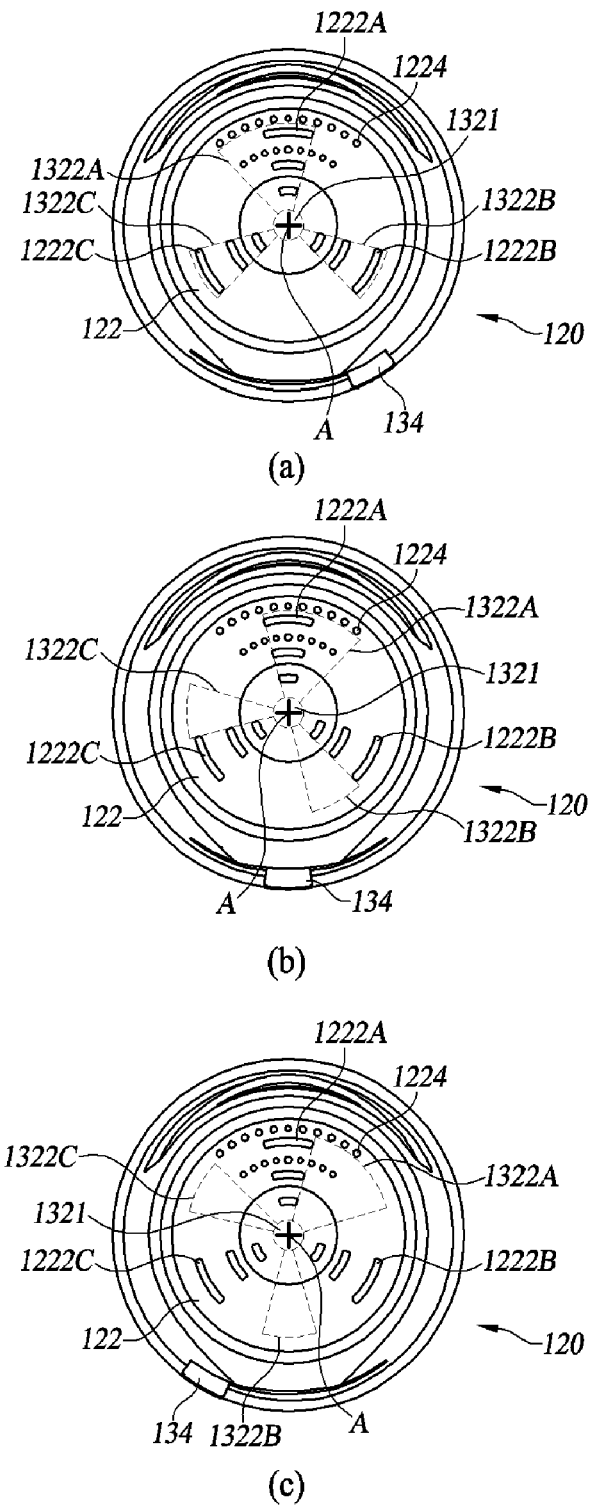
FIG. 7 shows diagrams of a positional relationship between a jetting region adjusting portion and multiple jetting holes according to one embodiment of the present disclosure.

FIG. 7 shows diagrams of a positional relationship between a jetting region adjusting portion 130 and multiple jetting holes 1222 according to one embodiment of the present disclosure.

Specifically, (a), (b), and (c) in FIG. 7 indicate the positions of the jetting region adjusting portion 130 when it is in the first position, the second position, and the third position, respectively.

As shown in (a), (b), and (c) in FIG. 7, the disk 132 may be configured to be rotatable with respect to the head 120 about the axis of rotation 'A' passing through the head 120.

The jetting region adjusting portion 130 may have a first position, a second position, and a third position according to the degree of rotation of the disk 132 with respect to the head 120.

In the first position, expulsion of the shaving aid from all of the multiple jetting holes 1222 may not be blocked.

Further, in the second position, expulsion of the shaving aid from at least some of the multiple jetting holes 1222 may not be blocked.

Furthermore, in the third position, expulsion of the shaving aid from all of the multiple jetting holes 1222 may be blocked.

Here, blocking of the expulsion of the shaving aid refers to closing at least a portion of the flow path of the shaving aid, from the spraying portion 116 of the containing portion 110 to the jetting holes 1222.

Therefore, even when the spraying actuating portion 140 is in the spraying position, no shaving aid is expelled from the jetting hole 1222 that allows blocking of the expulsion of the shaving aid.

The multiple jetting holes 1222 may include at least one first jetting hole 1222A having a first height H1 and at least one second jetting hole 1222B having a second height H2 that is less than the first height H1, as shown in FIG. 4.

Specifically, the first jetting hole 1222A may be located adjacent to the edge region 'E' of the head 120 on the inclined aid applying surface 122, and conversely, the second jetting hole 1222B may be located in an area opposite the head 120.

The disk 132 of the jetting region adjusting portion 130 may have a first flow channel 1322A having a first size and a second flow channel 1322B having a second size that is smaller than the first size.

The first flow channel 1322A may communicate, in its first position and second position, with the first jetting hole 1222A. The second flow channel 1322A may communicate, in its first position, with the second jetting hole 1222B.

Specifically, as shown in (a) of FIG. 7, in the first position, the first flow channel 1322A and the second flow channel 13228 may communicate with the first jetting hole 1222A and the second jetting hole 12228, respectively.

Therefore, in the first position, when there is a spraying operation by the spraying actuating portion 140, the shaving aid may be expelled from both the first jetting hole 1222A and the second jetting hole 12228.

As shown in (b) of FIG. 7, the lever 134 in the first position, when rotated in the clockwise direction, will turn the disk 132 in the same clockwise direction, whereby the spraying actuating portion 140 may be located in the second position.

In the second position, the first flow channel 1322A having the first size may still communicate with the first jetting hole 1222A, but the second flow channel 13228 having a second size smaller than the first size may not communicate with the second jetting hole 12228 as the disk 132 rotates.

Therefore, in the second position, when there is a spraying operation by the spraying actuating portion 140, the shaving aid may be expelled only through the first jetting hole 1222A, and may not be ejected through the second jetting hole 12228.

At this time, the shaving aid may be expelled in the region adjacent to the first jetting hole 1222A which is positioned adjacent to the edge region 'E' of the head 120. This allows the user to apply the shaving aid selectively expelled to the edge area E on a relatively narrow area, such as an area under a nose.

As shown in (c) of FIG. 7, the lever 134 in the second position, when rotated in the clockwise direction, will turn the disk 132 in the same clockwise direction, whereby the spraying actuating portion 140 may be located in a third position.

In the third position, the first flow channel 1322A and the second flow channel 13228 may not be in communication with both the first jetting hole 1222A and the second jetting hole 12228.

Thus, in the third position, when there is a spraying operation by the spraying actuating portion 140, no shaving aid may be expelled from both the first jetting hole 1222A and the second jetting hole 12228.

The shaving aid application apparatus 10 according to one embodiment of the present disclosure may selectively block each jetting hole of the multiple jetting holes 1222 through the jetting region adjusting portion 130, whereby selectively adjusting the amount of shaving aid expelled from the jetting holes.

In addition, the shaving aid application apparatus 10 according to one embodiment is configured to expel the shaving aid only in the edge region 'E' of the head 120, in the second position, thereby allowing a targeted application of the shaving aid on a relatively narrow skin area, which is convenient for the user.

Figure 8:
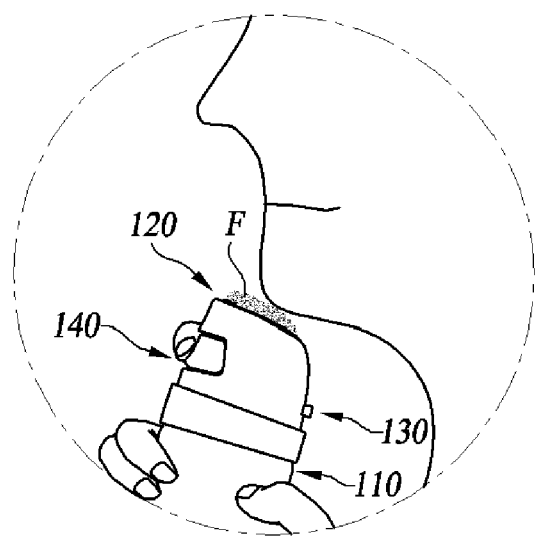
FIG. 8 shows diagrams of a user applying a shaving aid by using a shaving aid application apparatus according to one embodiment of the present disclosure.
Figure 8:
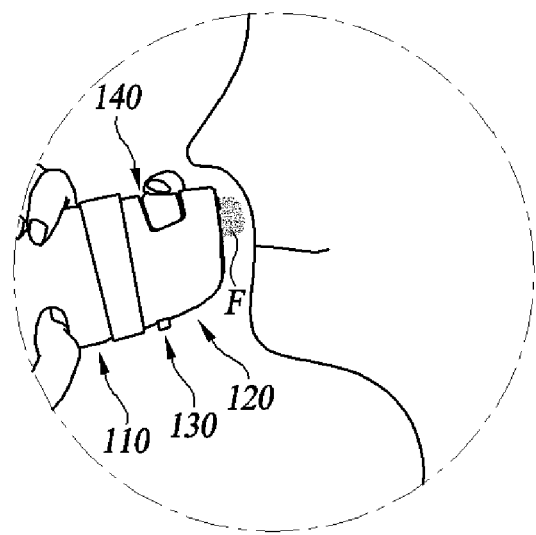

FIG. 8 shows diagrams of a user applying a shaving aid 'F' by using a shaving aid application apparatus 10 according to one embodiment of the present disclosure.

Specifically, (a) of FIG. 8 illustrates the application of shaving aid 'F' to the user's jaw, and (b) of FIG. 8 illustrates the application of shaving aid 'F' to an area under the user's nose.

As shown in (a) of FIG. 8, the user may perform a spraying operation with the jetting region adjusting portion 130 being in the first position.

In this case, the shaving aid 'F' may be expelled from both the first jetting hole 1222A and the second jetting hole 1222, thereby expelling the shaving aid 'F' evenly throughout the aid applying surface 122.

The shaving aid 'F' evenly expelled throughout the aid applying surface 122 may be applied to a relatively large area of skin, for example, the user's chin.

As shown in (b) of FIG. 8, the user may perform a spraying operation with the jetting region adjusting portion 130 being in the second position.

Here, the shaving aid 'F' may be expelled from the first jetting hole 1222A adjacent to the edge region 'E' of the head 120, while no shaving aid 'F' may be expelled from the second jetting hole 1222 located in the opposite region of the head 120.

Thus, on the aid applying surface 122, only the edge region 'E' of the head 120 having a relatively small angle may allow the shaving aid 'F' to be sprayed.

The controlled expulsion of the shaving aid 'F' from a portion of the aid applying surface 122 may be applied to a relatively narrow skin area, for example, an area under the nose of the user.

The shaving aid application apparatus 10 according to one embodiment may selectively adjust the jetting holes 1222 through which the shaving aid 'F' is expelled, thereby providing the user with an appropriate application function depending on the skin area to be applied with the shaving aid 'F'.

Figure 9:
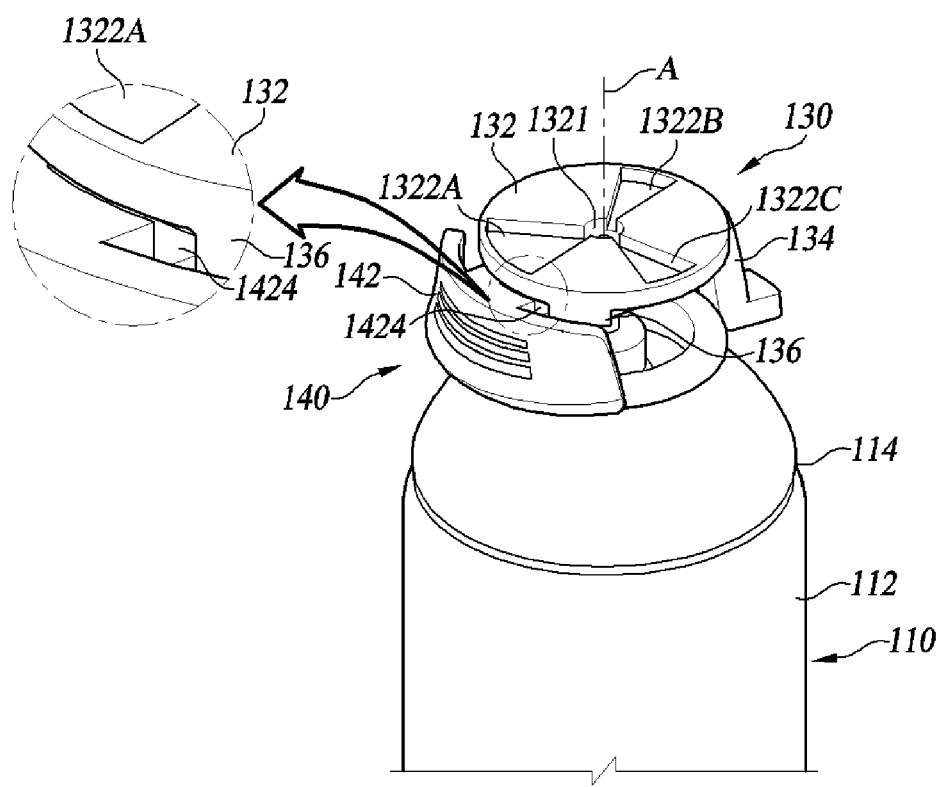
FIG. 9 is a diagram of a jetting region adjusting portion of a shaving aid application apparatus in a second position according to one embodiment of the present disclosure.

FIG. 9 is a diagram of the jetting region adjusting portion 130 in the second position according to one embodiment of the present disclosure. In FIG. 9, the head 120 is omitted for convenience of description.

As shown in FIG. 9, when the jetting region adjusting portion 130 is in a second position, the locking protrusion 136 of the disk 132 may be completely removed from the locking groove 1424 of the button portion 142.

In this case, the button portion 142 may move freely in the first direction, and thus, the spraying actuating portion 140 may reside in between the spraying position and the rest position.

FIG. 9 illustrates a case where the jetting region adjusting portion 130 is in the second position. However, the description of FIG. 9 also applies to a case where the jetting region adjusting portion 130 is in the first position.

Figure 10:
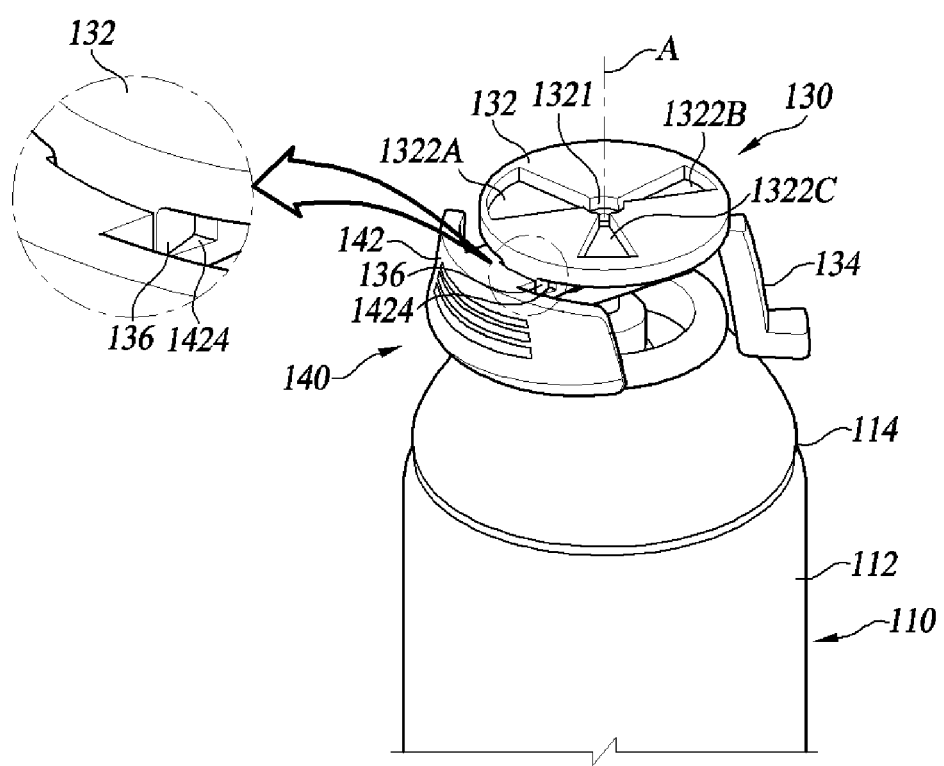
FIG. 10 is a diagram of a jetting region adjusting portion of a shaving aid application apparatus in a third position according to one embodiment of the present disclosure.

FIG. 10 is a diagram of the jetting region adjusting portion 130 in a third position according to one embodiment of the present disclosure. In FIG. 10, the head 120 is omitted for convenience of description.

Figure 11:
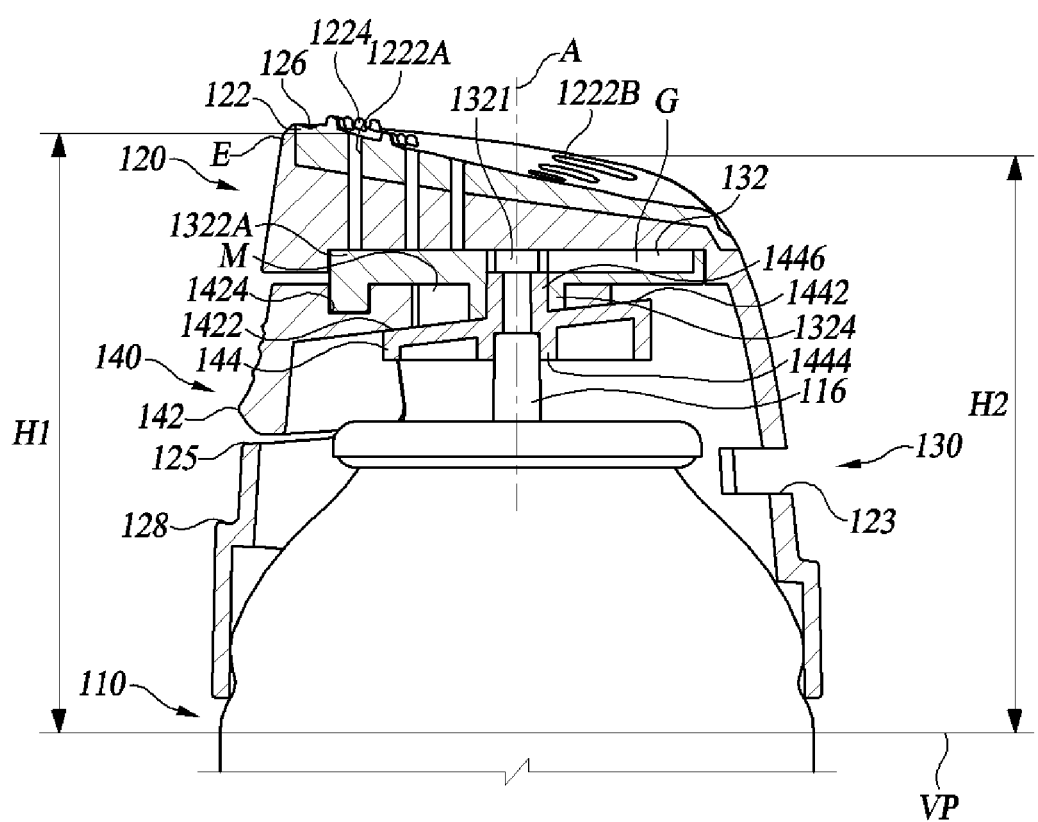
FIG. 11 is a side cross-sectional view of the shaving aid application apparatus shown in FIG. 10.

FIG. 11 is a side sectional view of the shaving aid application apparatus 10 shown in FIG. 10.

As shown in FIGS. 10 and 11, when the jetting region adjusting portion 130 is in the third position, the locking protrusion 136 of the disk 132 may be inserted at least partially into the locking groove 1424 of the button portion 142.

In this case, the button portion 142 may be prevented from moving in the first direction by the locking protrusion 132 inserted into the locking groove 1424, and thus, the spraying actuating portion 140 may be fixed in the rest position.

The shaving aid application apparatus 10 according to one embodiment of the present disclosure is configured to automatically hold the operation of the button portion 142 when the multiple jetting holes 1222 are caused to completely block the expulsion of the shaving aid. In this way, with the jetting holes 1222 completely blocking the expulsion, the shaving aid application apparatus 10 can save the user from committing a spraying operation by mistake.

As described above, at least one embodiment of the present disclosure provides a shaving aid application apparatus which can apply a shaving aid in direct contact with the user's skin, thereby providing the user with a cleaner and easier application of the shaving aid.

Although exemplary embodiments of the present disclosure have been described for illustrative purposes, those skilled in the art will appreciate that various modifications, additions and substitutions are possible, without departing from the various characteristics of the disclosure. Therefore, exemplary embodiments of the present disclosure have been described for the sake of brevity and clarity. The scope of the technical idea of the present embodiments is not limited by the illustrations. Accordingly, one of ordinary skill would understand the scope of the disclosure is not limited by the above explicitly described embodiments but by the claims and equivalents thereof.

What is claimed is:

1. An apparatus comprising:
   a containing portion configured to hold a shaving aid;
   a head coupled to one side of the containing portion, an aid applying surface formed at one surface of the head;
   multiple jetting holes located at the aid applying surface; and
   a jetting region adjusting portion,
   wherein a spraying gap is defined between at least a portion of the containing portion and at least a portion of the head,
   wherein the shaving aid is expelled from the containing portion to pass through the spraying gap and provided through the multiple jetting holes,
   wherein the jetting region adjusting portion is disposed in the spraying gap and configured such that a jetting hole for expelling the shaving aid and a jetting hole not expelling the shaving aid are selectable from among the multiple jetting holes based on a position of the jetting region adjusting portion, and
   wherein:
   the jetting region adjusting portion is configured to have a first position, a second position, and a third position according to a degree of rotation of the jetting region adjusting portion with respect to the head;
   all the multiple jetting holes allow the expulsion of the shaving aid when the jetting region adjusting portion is in the first position;
   at least some of the multiple jetting holes block the expulsion of the shaving aid and others among the multiple jetting holes allow the expulsion of the shaving aid when the jetting region adjusting portion is in the second position; and
   all the multiple jetting holes block the expulsion of the shaving aid when the jetting region adjusting portion is in the third position.

2. The apparatus of claim 1, wherein the aid applying surface comprises at least a portion of a concave surface having the multiple jetting holes.

3. The apparatus of claim 2, wherein the at least a portion of the concave surface is made of a rubber material.

4. The apparatus of claim 2, wherein the concave surface comprises a comb portion having a plurality of protrusions.

5. The apparatus of claim 1, wherein the head further comprises:
   a first prevention protrusion configured to prevent at least a portion of the shaving aid expelled from the multiple jetting holes from flowing down from the aid applying surface; and
   a second prevention protrusion configured to prevent at least a portion of the shaving aid from the aid applying surface from flowing down on an outer peripheral surface of the containing portion.

6. The apparatus of claim 1, wherein the aid applying surface is inclined with respect to a virtual plane perpendicular to a height direction of the containing portion, and
   wherein the multiple jetting holes comprise a first jetting hole having a first height and a second jetting hole having a second height that is less than the first height.

7. The apparatus of claim 6, wherein the jetting region adjusting portion comprises a first flow channel having a first size and a second flow channel having a second size that is smaller than the first size, and
   wherein the first flow channel is in communication with the first jetting hole when the jetting region adjusting portion is in the first position or the second position, and
   wherein the second flow channel allows the second jetting hole and the containing portion to communicate with each other when the jetting region adjusting portion is in the first position.

8. The apparatus of claim 6, further comprising:
   a spraying actuating portion having a spraying position at which the shaving aid is sprayed from the containing portion and a rest position at which the shaving aid is not sprayed from the containing portion,
   wherein the spraying actuating portion is fixed to the rest position when the jetting region adjusting portion is in the third position.

9. The apparatus of claim 8, wherein the spraying actuating portion comprises:
   a button portion having a first inclined surface on one surface and configured to be movable in a first direction with respect to the head; and
   a pumping portion having a second inclined surface configured to cooperate with the first inclined surface such that the pumping portion is movable in a second direction that is not parallel to the first direction with respect to the head,
   wherein the spraying actuating portion is configured to be in one of the spraying position and the rest position according to a degree of movement of the pumping portion in the second direction, and
   the first inclined surface and the second inclined surface are configured to generate the cam motion as the button portion moves in the first direction.

10. The apparatus of claim 9, wherein the button portion is disposed adjacent to the first jetting hole.

11. An apparatus comprising:
    a containing portion configured to hold a shaving aid;
    a head coupled to one side of the containing portion, an aid applying surface formed at one surface of the head;
    multiple jetting holes located at the aid applying surface; and
    a jetting region adjusting portion,
    wherein a spraying gap is defined between at least a portion of the containing portion and at least a portion of the head,
    wherein the shaving aid is expelled from the containing portion to pass through the spraying gap and provided through the multiple jetting holes,
    wherein the jetting region adjusting portion is disposed in the spraying gap and configured such that a jetting hole for expelling the shaving aid and a jetting hole not expelling the shaving aid are configured such that a number of jetting holes for expelling the shaving aid among the multiple jetting holes is adjustable based on a position of the jetting region adjusting portion, and
    wherein the multiple jetting holes comprise a first jetting hole having a first height and a second jetting hole having a second height that is less than the first height such that the shaving aid is expelled through the first jetting hole at a height higher than the shaving aid expelled through the second jetting hole.

\* \* \* \* \*